(12) United States Patent
Lessick

(10) Patent No.: US 8,155,264 B2
(45) Date of Patent: Apr. 10, 2012

(54) GATED COMPUTED TOMOGRAPHY

(75) Inventor: Jonathan Lessick, Haifa (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 12 days.

(21) Appl. No.: 12/516,609

(22) PCT Filed: Nov. 13, 2007

(86) PCT No.: PCT/IB2007/054612
§ 371 (c)(1),
(2), (4) Date: May 28, 2009

(87) PCT Pub. No.: WO2008/065566
PCT Pub. Date: Jun. 5, 2008

(65) Prior Publication Data
US 2010/0040193 A1 Feb. 18, 2010

Related U.S. Application Data

(60) Provisional application No. 60/867,861, filed on Nov. 30, 2006.

(51) Int. Cl.
A61B 6/00 (2006.01)

(52) U.S. Cl. ................................. 378/8; 378/4

(58) Field of Classification Search ........................ 378/8
See application file for complete search history.

(56) References Cited

U.S. PATENT DOCUMENTS

| | | | | |
|---|---|---|---|---|
| 4,547,892 | A * | 10/1985 | Richey et al. | 378/8 |
| 6,510,337 | B1 * | 1/2003 | Heuscher et al. | 600/428 |
| 2003/0007593 | A1 * | 1/2003 | Heuscher et al. | 378/4 |
| 2003/0016851 | A1 * | 1/2003 | Kaufman et al. | 382/131 |
| 2004/0042581 | A1 * | 3/2004 | Okerlund et al. | 378/4 |
| 2004/0077941 | A1 * | 4/2004 | Reddy et al. | 600/428 |
| 2004/0120446 | A1 * | 6/2004 | Londt et al. | 378/4 |
| 2005/0089133 | A1 * | 4/2005 | Tsuyuki | 378/8 |
| 2006/0280283 | A1 * | 12/2006 | Hsieh et al. | 378/8 |
| 2007/0032735 | A1 * | 2/2007 | Bruder et al. | 600/523 |

FOREIGN PATENT DOCUMENTS

| | | |
|---|---|---|
| JP | 2003164446 A | 10/2003 |
| WO | 02103639 A2 | 12/2002 |
| WO | 03002002 A2 | 1/2003 |
| WO | 2005008597 A2 | 1/2005 |

OTHER PUBLICATIONS

Rasche, V., et al.; Automatic Selection of the Optimal Cardiac Phase for Gated Three-dimensional Coronary x-ray Angiography; 2006; Acad Radiol; 13:630-640.

Kovacs, A., et al.; CT-Coronary Angiography in Patients with Atrial Fibrillation; 2005; Fortschr Roentgenstr.;pp. 1655-1662.

Cademartiri, F., et al.; Improving Diagnostic Accuracy of MDCT Coronary Angiography in Patient with Mild Heart Rhythm Irregularities Using ECG Editing; 2006; AJR; pp. 634-638.

Appendix I: Mild Heart Rhythm Irregularities: Definition and Management; 2006; AJR; pp. 1-3.

* cited by examiner

Primary Examiner — Alexander H Taningco

(57) ABSTRACT

A computed tomography system (100) includes a windowing component (140) that receives an ECG signal that includes a premature heart cycle. The ECG signal is time-synchronized with x-ray projection data of a beating heart. The windowing component (140) either removes or repositions a first reconstruction window within a first heart cycle to correspond to a desired cardiac phase when the premature heart cycle causes the first reconstruction window to correspond to a different cardiac phase, based on available data. A reconstructor (148) that reconstructs projection data corresponding to a plurality of reconstruction windows from different cardiac cycles generates image data indicative of the desired phase of the heart.

31 Claims, 9 Drawing Sheets

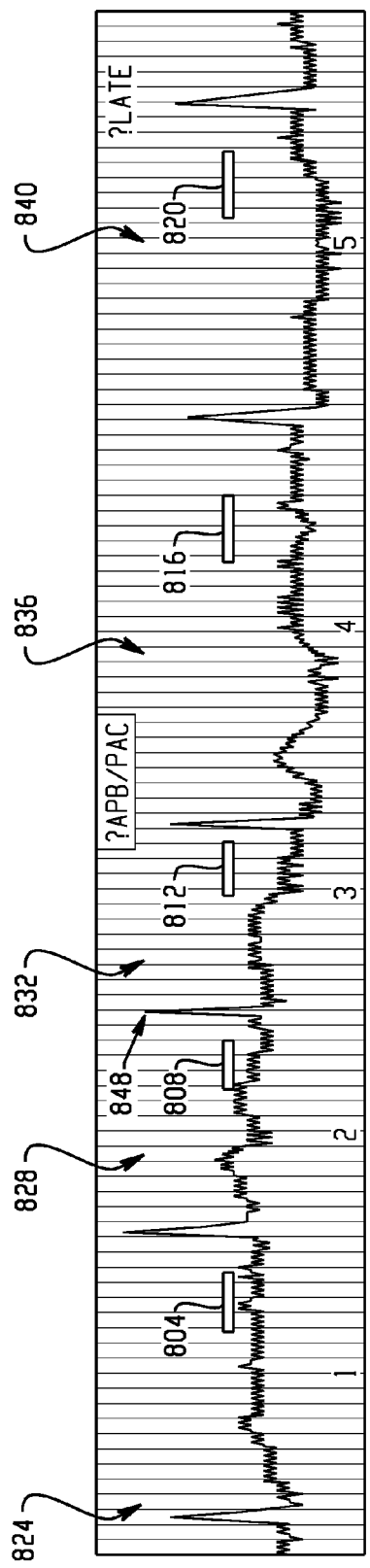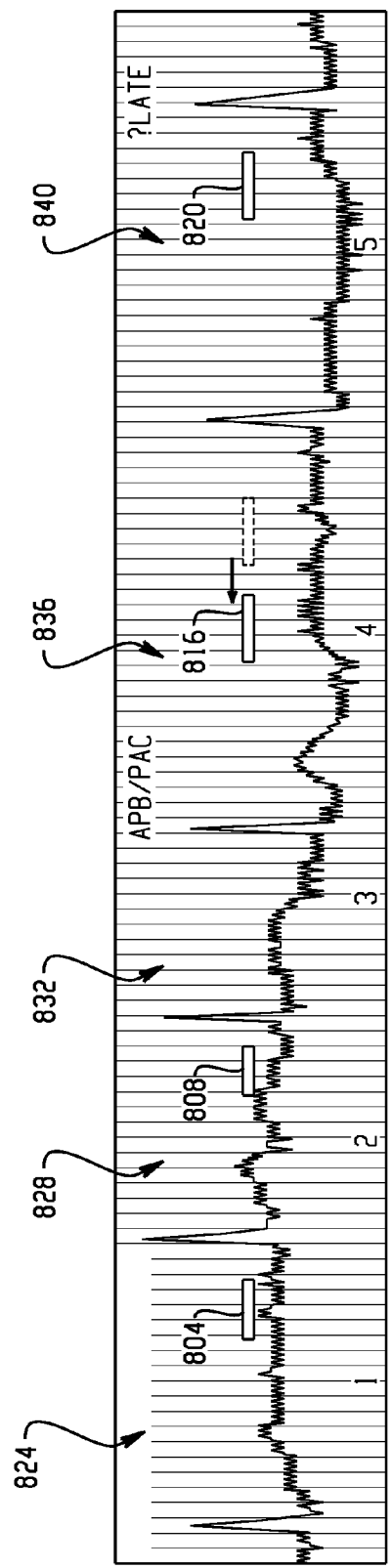

GATED COMPUTED TOMOGRAPHY

CROSS REFERENCE TO RELATED APPLICATIONS

This application claims the benefit of U.S. Provisional Application No. 60/867,861 filed on Nov. 30, 2006, which is incorporated herein by reference.

DESCRIPTION

The present application generally relates to imaging systems. In particular, it relates to computed tomography (CT) and, more particularly, to generating and detecting radiation and processing data indicative thereof.

Computed tomography (CT) imaging often includes scanning an object in motion. For example, cardiac CT imaging includes scanning a beating heart. With cardiac CT, it typically is more desirable to reconstruct data corresponding to a phase of the heart cycle in which the heart is relatively motionless. Various techniques including electrocardiogram (ECG) signal gating have been used to locate projection data corresponding to such a phase within projection data representative of the heart cycle(s).

With retrospective gating, electrical activity of the heart, which reflects the state of the heart throughout a heart cycle, is sensed by an electrocardiograph while a beating heart is scanned. Data corresponding to a desired heart phase is then gated (selected) and reconstructed based on the signal representing the electrical activity. The data is selected to obtain projection data collected over an angular range that provides a complete CT data set.

In one instance, the cardiac scanning procedure detects projection data over multiple successive heart cycles. A subset of data for each heart cycle corresponding to the desired phase is then selected for reconstruction. Reconstructing data from multiple heart cycles can improve temporal resolution. However, an irregular heart rhythm, which generally is unpredictable, can change one or more heart cycles relative to the average heart cycle. This may result in the selection of data corresponding to a different cardiac phase. As a consequence, the reconstructed image data may be degraded.

One attempt to improve the quality of such data is discussed in Cademartiri F. et al., *Improving diagnostic accuracy of MDCT coronary angiography in patients with mild heart rhythm irregularities using ECG editing*, AJR Am J Roentgenol. 2006 March;186(3):634-8. Cademartiri F. et al. describes a manual technique in which a user deletes a window that identifies data for reconstruction for a heart cycle if the heart cycle is followed by a premature heart cycle and, if this results in insufficient data for reconstruction, adds such a window(s) to the premature heart cycle. Unfortunately, the quality of resulting image data may be less than desired based on the available data.

Aspects of the present application address the above-referenced matters and others.

According to one aspect, a system includes a computed tomography system includes a windowing component that receives an ECG signal that includes a premature heart cycle. The ECG signal is time-synchronized with x-ray projection data of a beating heart. The windowing component positions a first reconstruction window within a first heart cycle to correspond to a desired cardiac phase when the premature heart cycle causes the first reconstruction window to correspond to a different cardiac phase. A reconstructor reconstructs projection data corresponding to a plurality of reconstruction windows from different cardiac cycles to generate image data indicative of the desired phase of the heart.

According to another aspect, a system includes a windowing component that deletes a first reconstruction window that corresponds to a suboptimal cardiac phase due to an anomalous signal in an ECG signal. The ECG signal is mapped in time with x-ray projection data of a beating heart over a plurality of heart cycles. The windowing component adds a replacement reconstruction window to optimize the reconstruction data set based on the anomalous signal and available projection data. A reconstructor reconstructs the reconstruction data set to generate image data indicative of the desired phase of the heart.

According to another aspect, a system includes a recommendation component that recommends a reconstruction window for a cardiac phase within a plurality of successive heart cycles based on an ECG signal and an arrhythmia therein. The ECG signal is obtained while concurrently scanning a beating heart with a computed tomography scanner. A reconstructor reconstructs data corresponding to the data for each cycle corresponding to the reconstruction window.

According to another aspect, a system includes a windowing component that automatically repositions or removes a first reconstruction window for a heart cycle based on a premature heart cycle within an ECG that is signal synchronized with x-ray projection data of a beating heart. A recommendation component automatically recommends at least one additional reconstruction window based on the premature heart cycle. A reconstructor reconstructs data corresponding to the reconstruction windows.

According to another aspect, a method includes receiving an ECG signal including a premature heart cycle, wherein the ECG signal is time-synchronized with x-ray projection data of a beating heart over multiple heart cycles, relocating a first reconstruction window within a first heart cycle that corresponds to data other than a desired cardiac phase due to the premature heart cycle, wherein each of a plurality of heart cycles includes a reconstruction window; and reconstructing the projection data corresponding to the plurality of reconstruction windows to generate image data indicative of the desired phase of the heart.

According to another aspect, a computer readable storage medium containing instructions which, when executed by a computer, cause the computer to carry out the method of receiving an ECG signal including a premature heart cycle, relocating a first reconstruction window within a first heart cycle that corresponds to data other than a desired cardiac phase due to the premature heart cycle, and reconstructing the projection data corresponding to the plurality of reconstruction windows to generate image data indicative of the desired phase of the heart.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 illustrates an exemplary imaging system.
FIG. 2 illustrates a representative ECG signal.
FIG. 3 illustrates a representative ECG signal having an anomalous heart cycle.
FIGS. 4a, 4b, 4c, 4d, 4e, 5a, 5b, 5c, 5d, and 5e provide examples in which the system uses the ECG signal having the anomalous heart cycle to select reconstruction data.

Figure 10:
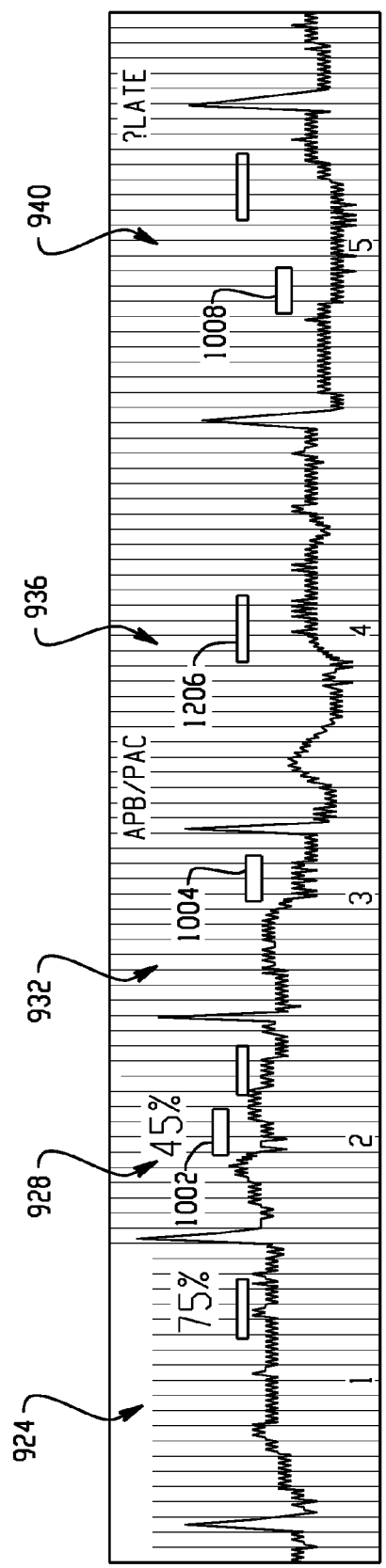

FIGS. 8, 9, and 10 graphically illustrate an exemplary method.

Figure 1:
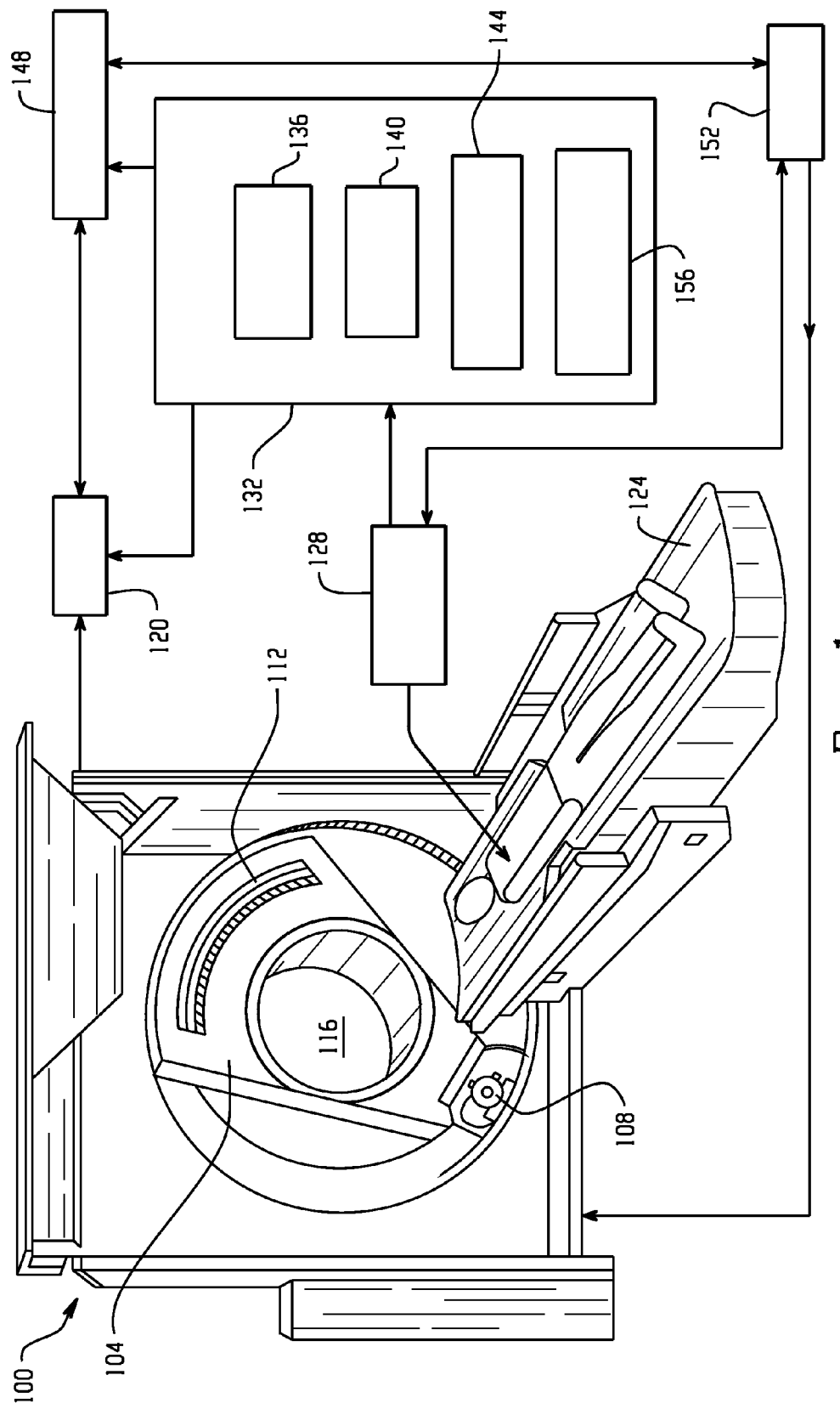

With reference to FIG. 1, a computed tomography (CT) scanner 100 includes a rotating gantry portion 104 which rotates about a longitudinal or z-axis. The portion 104 supports an x-ray source 108 such as a x-ray tube, and an x-ray detector 112, which generates x-ray projection data at a plurality of projection angles or views with respect to an examination region 116. The detector 112 includes a generally two-dimensional array of detector elements that generate output signals or projection data indicative of the detected radiation. A memory 120 or other storage device stores the projection data.

An object support 124 such as a couch supports a patient or other subject in the examination region 116. The object support 124 is movable so as to guide the patient or other subject within respect to the examination region 116 before, during, and after a scan.

A biological monitor 128, such as an electrocardiogram (ECG) or a respiratory monitor, provides information regarding the cardiac phase or other motion state of the subject. The biological monitor 128 signal, in the case of retrospective gating, is used to correlate the projection data with the motion phase or state at which it was acquired.

A processing component 132 communicates with the biological monitor 128 and facilitates selecting a set of reconstruction data from the projection data based on the biological signal. The processing component 132 includes an analyzing component 136, a windowing component 140, and a recommendation component 144. These components, individually or a combination thereof, facilitate selecting the set of reconstruction data when the biological signal includes an anomalous signal. In one instance, the set of data represents the optimal use of the available data in the presence of the anomalous signal.

In the case of cardiac CT, one example of such an anomalous signal is an arrhythmia or irregular rhythm such as a premature heart beat or extrasystole. In this case, the analyzing component 136 facilitates determining whether and how a reconstruction window is affected by a premature heart beat. If a reconstruction window is affected by the premature heart cycle, the windowing component 140 facilitates adjusting, removing, or adding one or more reconstruction windows based on the premature heart cycle. The recommendation component 144 recommends reconstruction window and cardiac phases based on the on the premature heart cycle and the available data. These components are described in greater detail below.

A reconstructor 148 reconstructs the selected projection data to generate image data. In the case of a retrospectively gated reconstruction, projection data corresponding to one or more desired motion states or phases of the subject or a region of interest thereof is reconstructed to generate image data corresponding to the desired cardiac phase(s).

A general purpose computer serves as an operator console 152. The console 152 includes a human readable output device such as a monitor or display and an input device such as a keyboard and mouse. Software resident on the console allows the operator to control and interact with the scanner 100. In one instance, the interaction includes presenting the biological signal to an operator, for example, by superimposing a reconstruction window identifying a cardiac phase with the biological signal. In addition, the interaction includes allowing the operator to manually identify an anomaly within the biological signal, generate a reconstruction window for a cardiac cycle, select or confirm a set of data for reconstruction, invoke automatic data selection and reconstruction, and otherwise interact with the scanner 100, for example, through a graphical user interface (GUI).

In the examples described below, the system 100 is used for a retrospective gated cardiac CT application. For this application, the biological monitor 128 provides an ECG signal that is synchronized with projection data corresponding to multiple heart beats.

Figure 2:
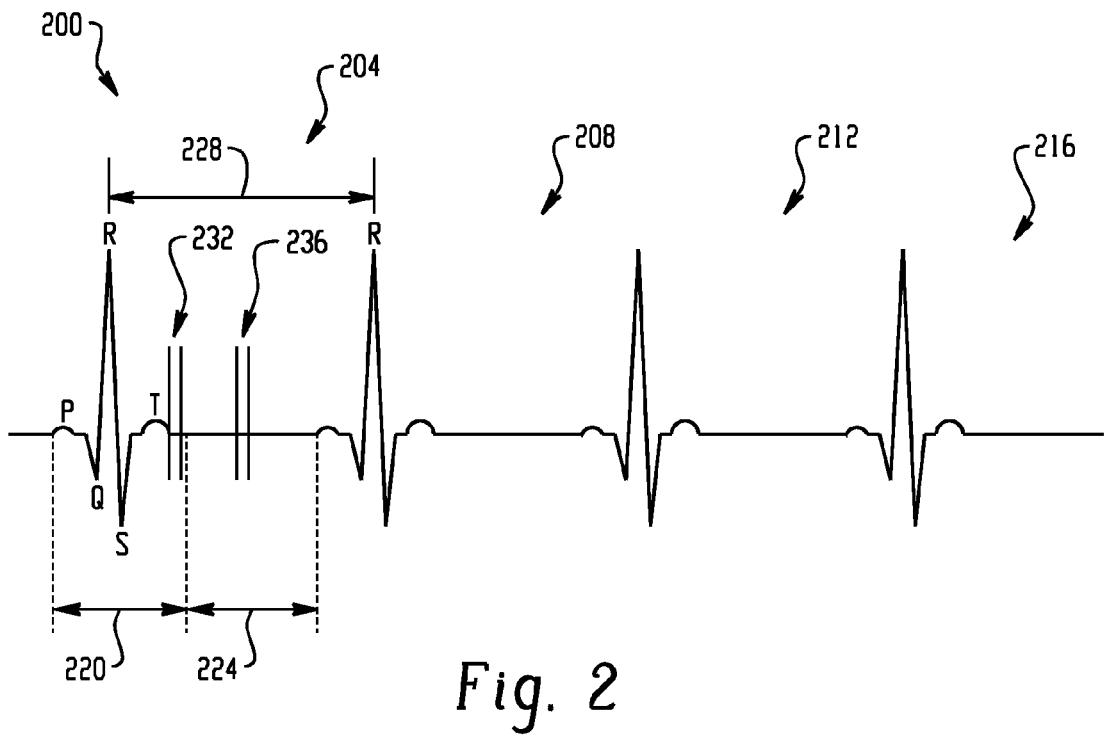

FIG. 2 illustrates a representative baseline ECG signal 200 that is "normal" in the sense that it does not include an extrasystole such as arrhythmia or irregular heart beat. Each of the heart cycles 204, 208, 212, and 216 includes a systolic period 220 in which the atria (the P wave) and subsequently the ventricles (the QRS complex) contract and the ventricles then re-polarize (the T wave), and a subsequent diastolic period 224 in which the heart relaxes after contraction and refills with circulating blood. The distance 228 between heart cycles or R-R intervals is represented by time period t. For explanatory purposes, in this example t is about one (1) second, and each of the systolic and diastolic periods represents about half of a heart cycle.

Assuming the baseline ECG signal 200 is recorded by the monitor 128, when the ECG signal 200 is received by the console 152, the console 152 displays the ECG signal 200 to the operator and provides a mechanism for the operator to select a desired cardiac phase for reconstruction or otherwise input information indicative of a desired cardiac phase. In one instance, the input invokes generation of a reconstruction window for different portions of the ECG signal 200, each corresponding to the desired cardiac phase.

By way of example, the operator may provide an input that leads to the generation of a reconstruction window for a "quiet" or relatively motionless cardiac phase of the diastolic period. One such phase generally occurs mid to end diastole. In one instance, this phase is approximated to be at about seventy (70) percent of the time duration of a heart cycle relative to the peak of the R wave. An exemplary reconstruction window 236 for this phase is shown in FIG. 2.

Another phase in which the heart is relatively motionless occurs at about the end of systole. This phase is approximated to be at about forty (40) percent of the time duration of the cycle. An exemplary reconstruction window 232 for this phase is also shown in FIG. 2. Other techniques for approximating the location of a cardiac phase within the ECG signal 200 such as, but not limited to, time based approaches are also contemplated herein. In addition, the operator may additionally or alternatively select a different cardiac phase.

In general, the width of a reconstruction window is configured so that the data acquired over the multiple revolutions provides a complete set of data (or at least one hundred and eighty (180) degrees plus a fan angle of data) for reconstruction. Since the ECG 200 is synchronized with the projection data, the reconstruction window identifies the projection data that corresponds to the desired cardiac phase.

In this example, the system is configured so that the data acquired during adjacent heart cycles overlap in the z-axis or longitudinal direction. The overlapping data acquisitions accommodates heart cycle time duration differences between adjacent heart cycles and mitigates data gaps, or instances in which there is a lack of data between reconstruction windows corresponding to adjacent heart cycles. System parameters such as table pitch are suitably configured based on the individual's average heart rate, the number and width of the detectors and the rotation speed in order to provide a suitable table speed for the overlapping data acquisitions.

Figure 3:
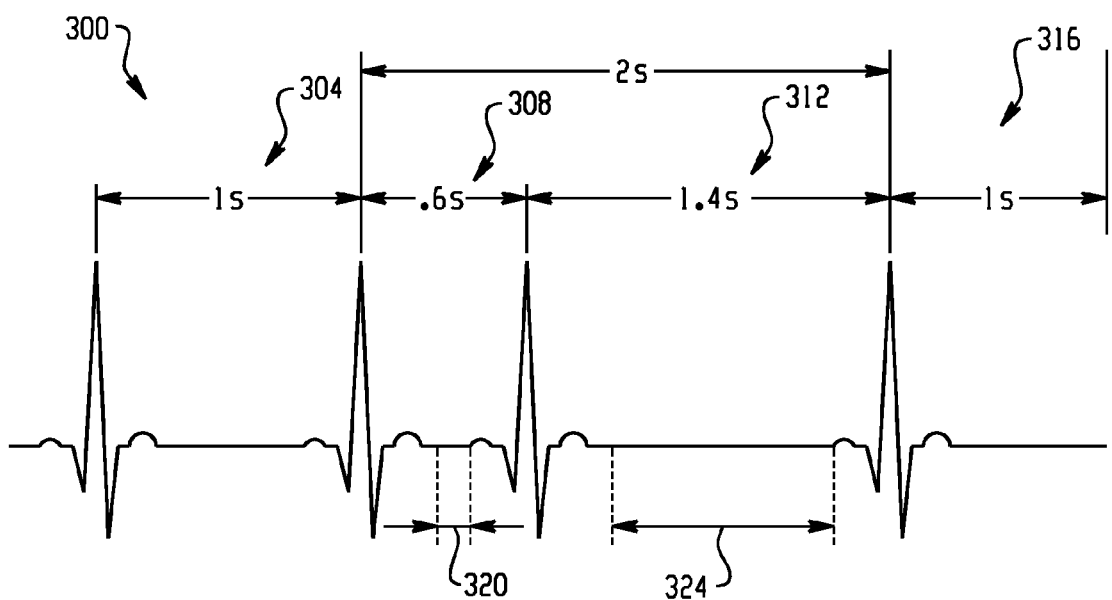

FIG. 3 illustrates an ECG signal 300 having a premature heart cycle 312. For this example the heart cycles 304, 308 and 316 are considered "normal" in the sense that they generally occur in time as expected (although they may be affected by the premature heart cycle 312 as discussed below) based on the one (1) second time duration intervals depicted in the heart cycles in FIG. 2.

The heart cycle 312 is premature in that it occurs earlier than expected. In this example, the premature heart cycle 312 occurs six tenths (0.6) of a second after the R wave of the heart cycle 308 instead of one (1) second. As a consequence, a diastolic period 320 of the second heart cycle 308 is shortened, or ends after six tenths (0.6) of a second instead of one (1) second after its corresponding R wave.

In addition, a diastolic 324 period of the premature heart cycle 312 is extended. In this example, the diastolic period of the premature heart cycle 312 is prolonged such that the distance from the R wave of the heart cycle 308 to the R wave of the next "normal" heart cycle, the heart cycle 316, is about the same distance as between two normal heart cycles, or about two (2) seconds.

The analyzing component 136, the windowing component 140, and the recommendation component 144 are now further described. In the following examples, assume that the ECG signal 300 having the premature heart cycle 312, the identification of the premature cycle 312, and the reconstruction windows and desired cardiac phase are provided to the processing component 132.

The analyzing component 136 determines the affect that the premature heart cycle 312 has on the data identified for reconstruction via the reconstruction window and desired cardiac phase. The heart cycles 304 and 316 are not affected by the premature heart cycle 312. As a result, the reconstruction windows within these heart cycles correspond to the desired cardiac phase.

In contrast, the heart cycles 308 and 312 are affected (as discussed above) in that the heart cycle 308 is shortened and the heart cycle 312 is extended. As a results, a reconstruction window positioned within the heart cycle 308 based on a percentage of the time duration of the heart cycle 308 is located relatively early in time within the heart cycle, and a reconstruction window positioned within the heart cycle 312 based on a percentage of the time duration of the heart cycle 312 is located relatively later in time within the heart cycle.

With respect to the heart cycle 308, the analyzing component 136 determines whether the reconstruction windows occurs prior to or after the premature heart cycle 312 in terms of time from the peak of its R wave.

Figure 4A:
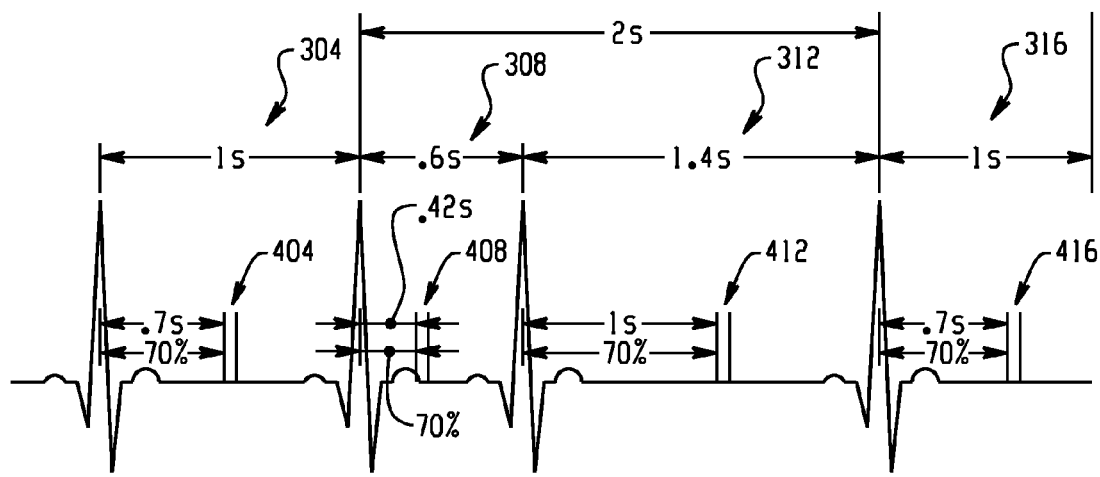

FIG. 4a illustrates a case in which a reconstruction window 408 within the heart cycle 308 is located, in time relative to a peak of the R wave, after the premature heart cycle 312. It is to be appreciated that a reference other than the peak of the R wave can alternatively be used.

As depicted, the premature heart cycle 312 occurs at about six tenths (0.6) of a second after the peak of the R wave for the heart cycle 308, and the reconstruction windows 404, 408, 412, and 416 are at about seventy (70) percent (%) of their corresponding heart cycle. As a result, in terms of time after the peak of the R wave the reconstruction window 408 is at about forty-two hundredths (0.42) of a second instead of at about seven tenths (0.7) of a second after the peak of the R wave, as is the reconstruction windows 404 and 416 within the unaffected heart cycles 304 and 316.

Figure 4B:
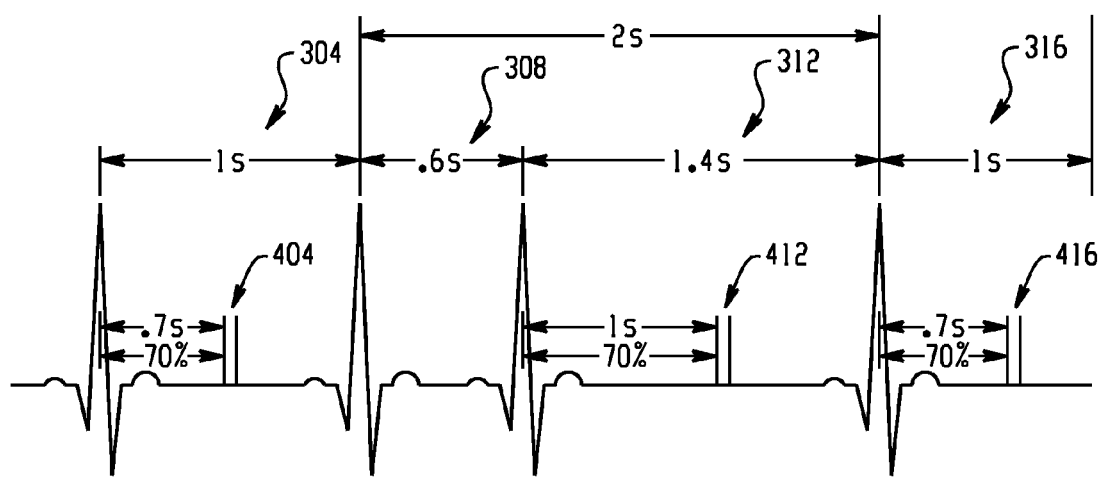

The analyzing component 136 recognizes that the reconstruction window 408 does not correspond to the desired cardiac phase and that the reconstruction data is suboptimal for reconstruction purposes since includes data corresponding to a different cardiac phase. The windowing component 140 removes the reconstruction window 408 so that the corresponding data is not selected for reconstruction or reconstructed. This is illustrated in FIG. 4b. In general, if a reconstruction window in time after the peak of its corresponding R wave occurs at or later than a premature heart cycle, then the reconstruction window is removed so that the corresponding data is not selected for reconstruction or reconstructed.

Figure 5A:
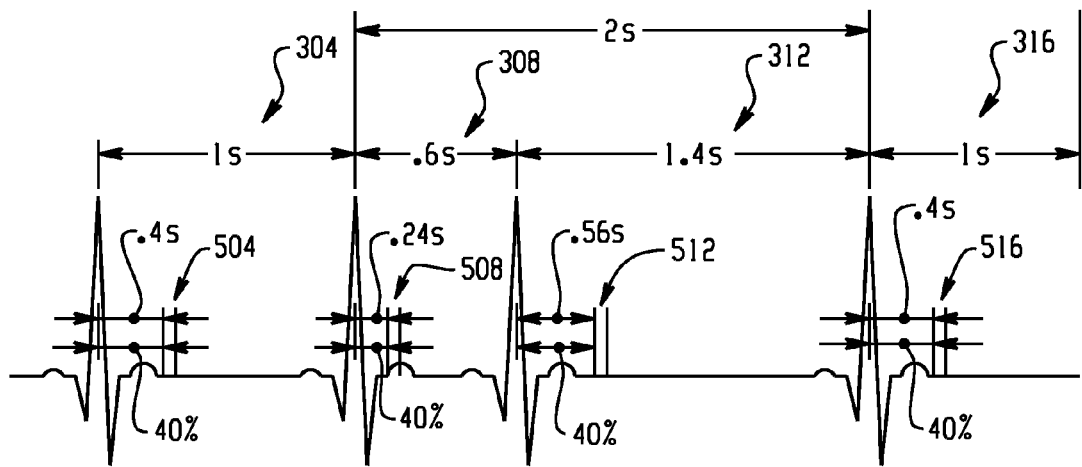

FIG. 5a illustrates the case in which a reconstruction window 508 within the heart cycle 308 is located, in time relative to the peak of the R wave, before the premature heart cycle 312.

As depicted, the premature heart cycle 312 occurs at about six tenths (0.6) of a second after the peak of the relevant R wave, and the reconstruction windows 504, 508, 512, and 516 are at about forty (40) percent (%) of their corresponding heart cycle. In terms of time after the peak of the R wave, the reconstruction window 508 is at about twenty-four hundredths (0.24) of a second after the peak of its corresponding R wave instead of at about four tenths (0.4) of a second after the peak of the R wave like the reconstruction windows 504 and 516 within the unaffected heart cycles 304 and 316.

The heart cycle 308 up to the occurrence of the premature heart cycle 312 is regular so the data within this region is normal, or is as if the premature heart cycle never occurred. The analyzing component 136 recognizes that the premature heart cycle 312 has caused the reconstruction window 508 to shift away from the desired cardiac phase, resulting in suboptimal reconstruction data.

Figure 5B:
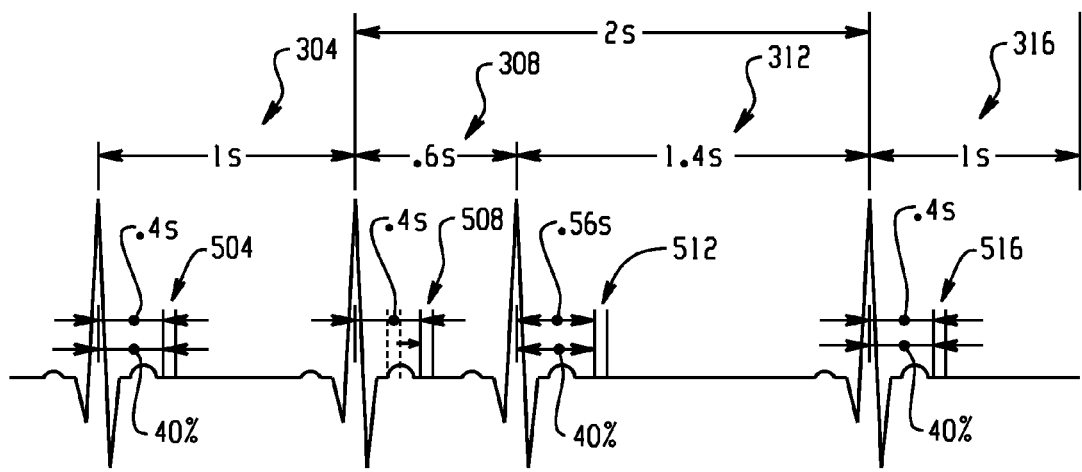

The windowing component 140 moves or positions the reconstruction window 508 in terms of time so that it is positioned from the peak of its R wave in terms of time rather than as a percentage of the cycle time duration. As a result, the reconstruction window is moved to a position at about four tenths (0.4) seconds from the R wave so that the reconstruction window 508 corresponds to the desired cardiac phase. This is illustrated in FIG. 5b.

Figure 4C:
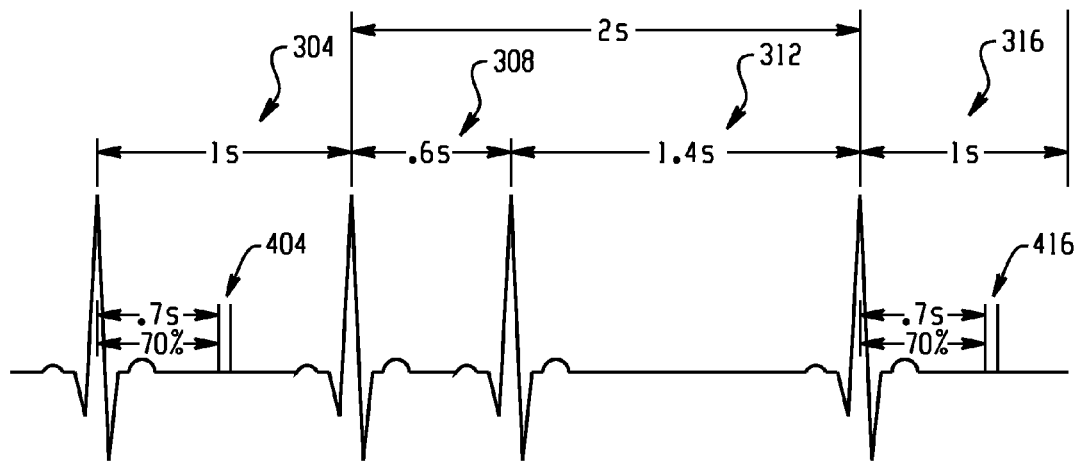
Figure 5C:
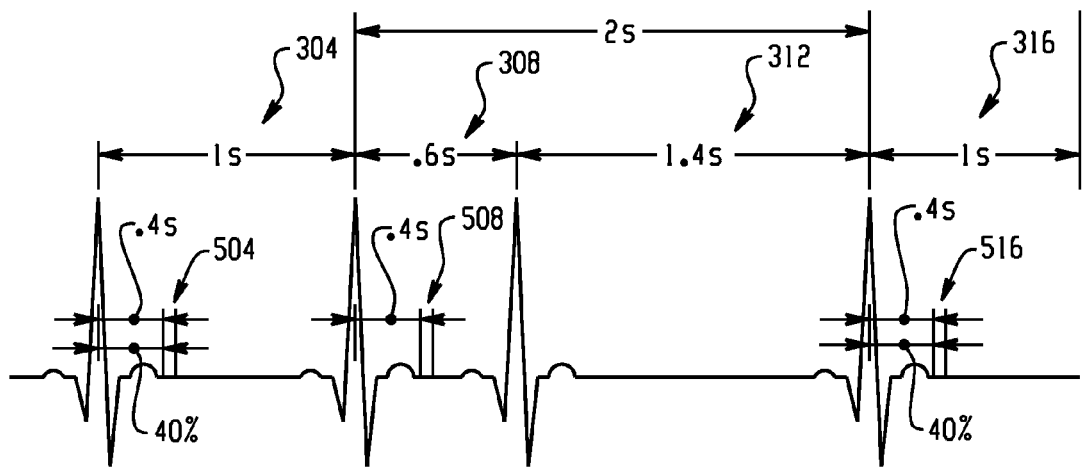

With respect to the premature heart cycle 312, the cycle 312 is always abnormal to some degree and therefore optimally it should be removed. The analyzing component 136 determines whether, after removing window 412 or 512, a data gap occurs. If there is no data gap, the window 412 or 512 is removed as illustrated in FIGS. 4c and 5c.

Figure 4D:
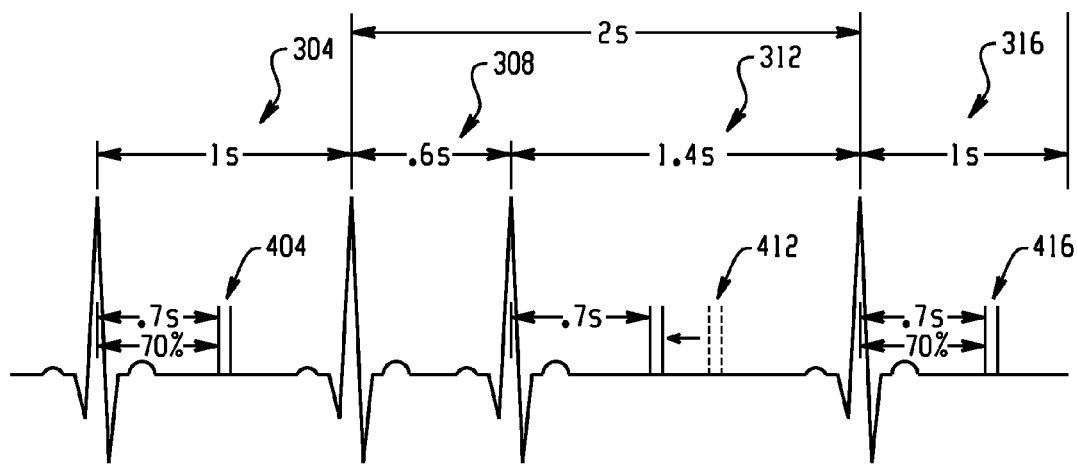
Figure 5D:
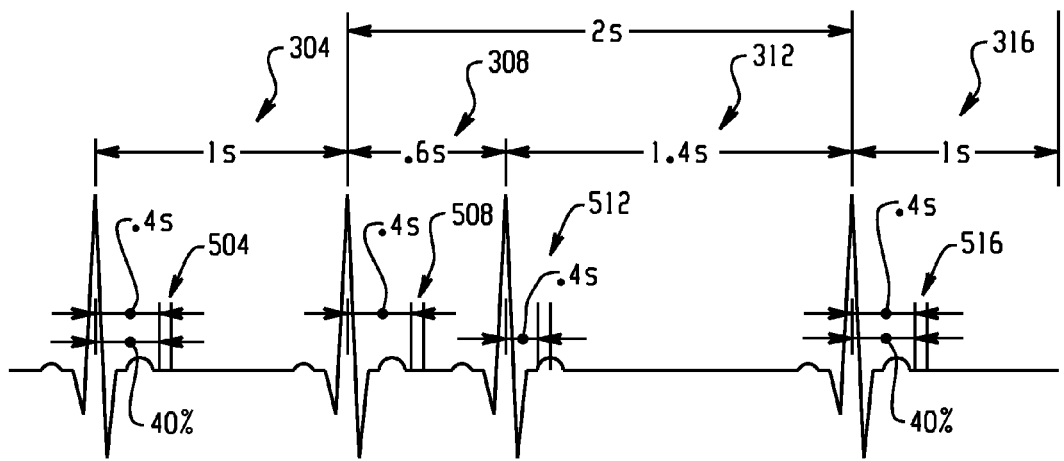

If there is a data gap, then the windowing component 140 makes optimal use of the data available. For an atrial extrasystole, the cycle 312 is approximately normal so the reconstruction window 412 is placed at about seven tenths (0.7) of a second from the R wave of cycle 312 as shown in FIG. 4d, and the reconstruction window 512 is placed at about four-tenths (0.28) of a second from the R wave of cycle 312 as shown in FIG. 5d.

Figure 4E:
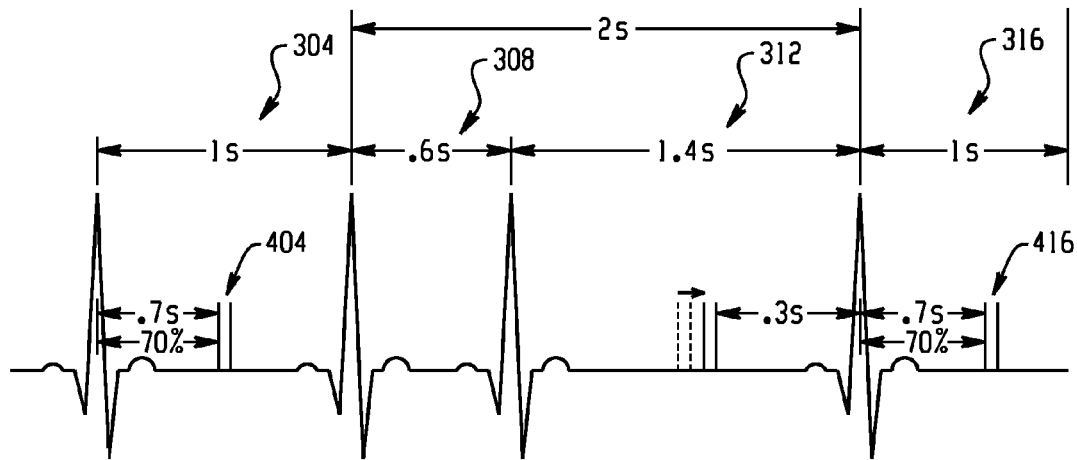
Figure 5E:
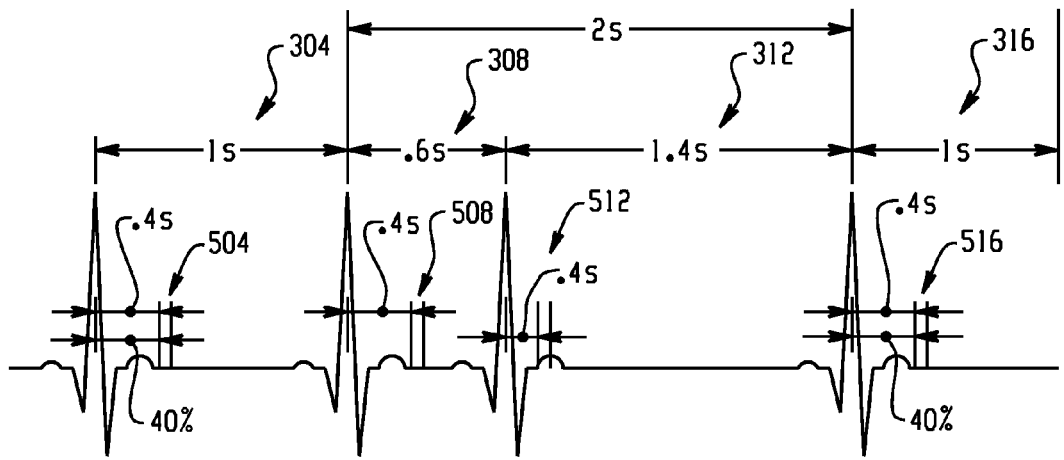

For a ventricular extrasystole, the cycle 312 is more abnormal. The window 412 is placed at about three tenths (0.3) of a second (1 second-0.7 seconds) before the next R as shown in FIG. 4e. The window 512 is placed at about four-tenths (0.28) of a second from the R wave of cycle 312 (like it is for an atrial extrasystole as described above) as shown in FIG. 5e.

The analyzing component 136 determines whether a data gap occurs if a window is removed by determining whether the data corresponding to the remaining reconstruction windows would provide sufficient data for reconstruction purposes so that there is no missing data. One technique for approximating whether sufficient data exists includes checking to see whether the inequality in Equation 1 is satisfied:

$$(T*TS)>(SC*T/RT),\quad \text{Equation 1}$$

wherein T represents the time interval, TS represents the table speed, SC represents the x-ray beam collimation, and RT represents the x-ray source rotation time. The time interval T is measured from the previous normal reconstruction window to the reconstruction window of the following normal heart cycle. If the product of the time interval and the scanner table speed is greater, then a data gap exists and there is not enough data to reconstruct the image at all z-axis locations.

Figure 6:
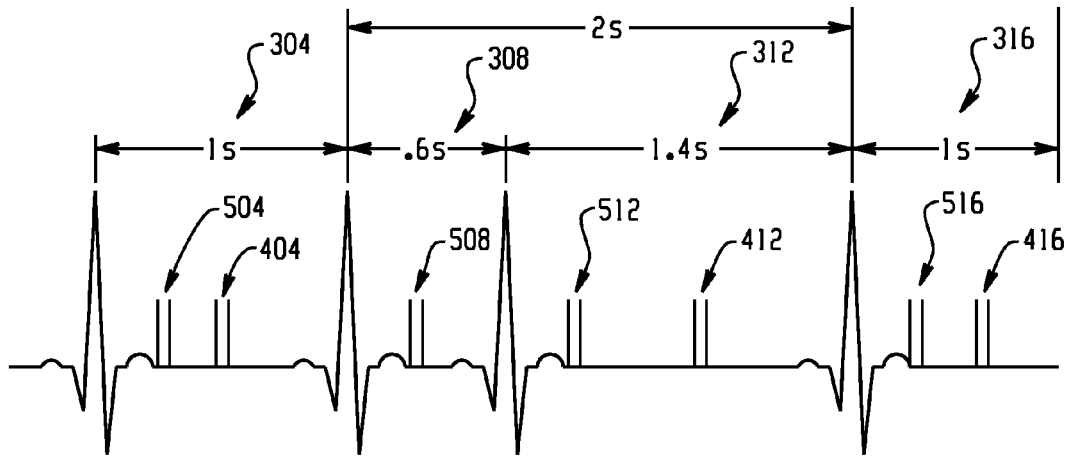
FIG. 6 illustrates an example in which a different phase for reconstruction is recommended.

If repositioning the seventy (70) percent (%) reconstruction windows as described above in connection with FIGS. 4d and 4e results in data gaps, then the recommendation component 144 provides a global recommendation. For the global recommendation, the recommendation component 144 recommends an entirely new reconstruction at a different phase (s) located before the premature R wave as shown in FIG. 6. In this example, the recommended phase is the forty (40) percent (%) phase depicted in FIG. 5a. This ensures a valid reconstruction window for the cycle 308 and provides the option to deciding whether to delete or relocate the reconstruction window for 312 and, thus, ensures having one or more reconstruction without data gaps. The seventy (70) percent (%) phase is reconstructed according to FIG. 4b-e and the new forty (40) percent (%) phase is reconstructed according to FIG. 5b-e.

Figure 7:
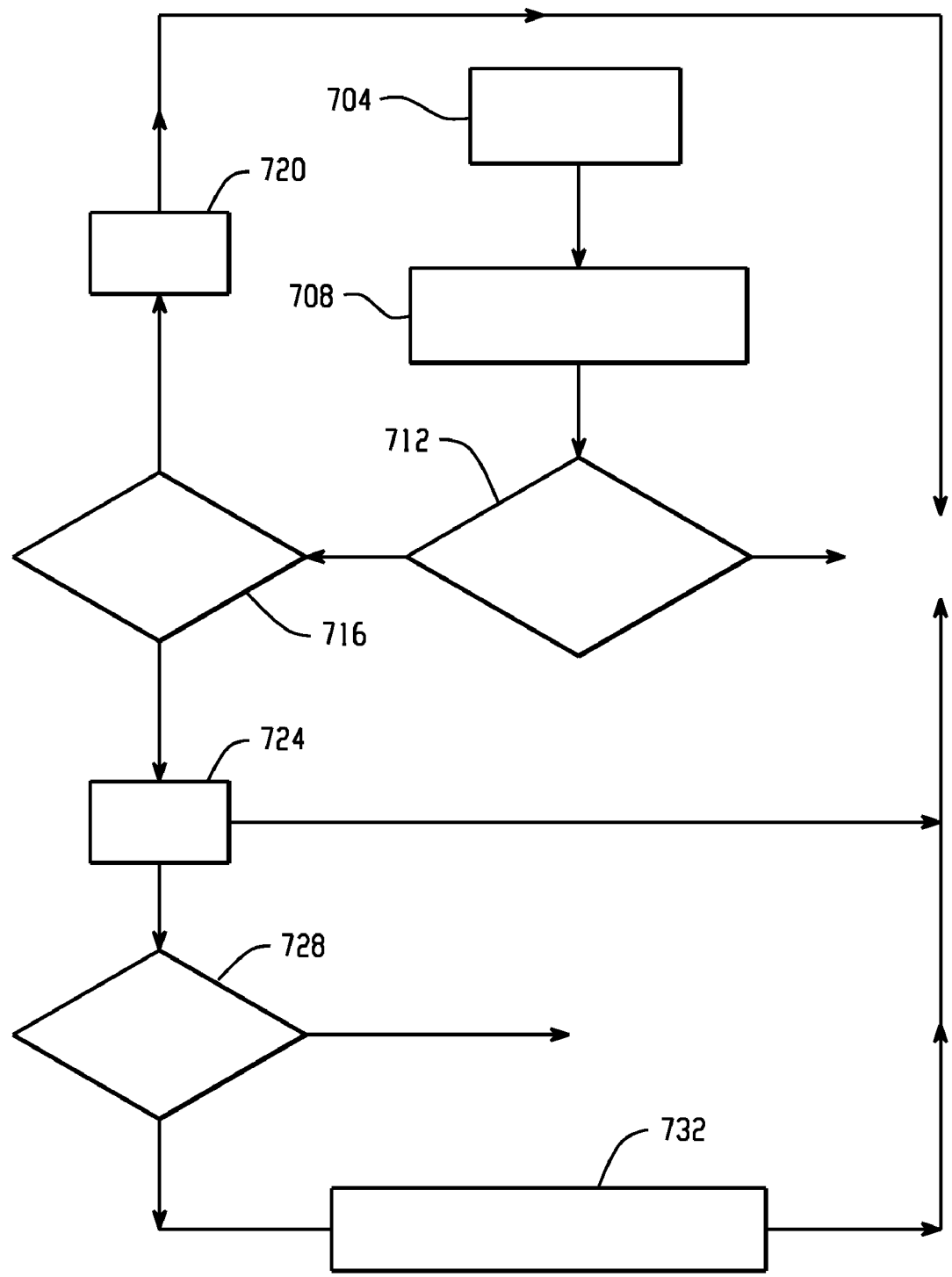
FIG. 7 illustrates an exemplary method.

FIG. 7 illustrates an exemplary method for selecting optimal reconstruction windows by the system 100. At 704, an ECG signal synchronized with projection data is obtained. At 708, an anomalous heart cycle such as a premature heart cycle is identified within the ECG signal, and a desired cardiac phase is selected for reconstruction. Based on this information, the processing component 128 determines optimal use of the available data in the presence of the anomaly in the heart signal.

At 712, the analyzing component 132 determines whether the anomaly results in a reconstruction window that corresponds to a cardiac phase other than the desired cardiac phase. If not, the reconstruction windows or the data corresponding to the reconstruction windows is selected for reconstruction.

However, if the anomaly affects the reconstruction data, then at 716 it is determined whether there is sufficient data so that an affected reconstruction window can be removed without introducing a data gap. If there is sufficient data, then at 720 the reconstruction window is removed, and the remaining reconstruction windows or the data corresponding thereto are selected for reconstruction.

Otherwise, at 724, the affected reconstruction window is moved as described above, and the reconstruction windows or the data corresponding thereto are selected for reconstruction.

At 728, it is determined whether moving the reconstruction window introduced a data gap. At 732, if a data has been introduced, then a new reconstruction with sufficient data is also recommended.

FIGS. 8, 9, and 10 graphically show an example. Initially referring to FIG. 8, an exemplary ECG signal with reconstruction windows 804, 808, 812, 816, and 820 covering phases located at about seventy-five (75) percent (%) respectively within each heart cycle 824, 828, 832, 836, and 840 as illustrated. The heart cycle 836 is identified as an atrial premature beat (APB).

In this example, the premature heart cycle 836 begins prior to the reconstruction window 812 when the reconstruction window 812 is expressed in terms of time from a peak of an R wave 848 of the heart cycle 832. Since the reconstruction windows 804-840 are positioned based on a percentage of the heart cycle and the heart cycle 832 is shortened, the reconstruction window 812 is suboptimal in that is does not correspond to the desired cardiac phase at seventy-five (75) percent of an average heart cycle. As a result, the reconstruction window 812 is removed, as illustrated in FIG. 9.

Premature heart cycle 836 is abnormal and therefore the system examines whether window 816 can be removed as well. Since this results in missing data, an alternative strategy is applied, and the reconstruction window 816 is relocated to a more optimal location as shown in FIG. 9 based on the time from the peak of the R wave of the premature heart cycle 836.

In this example, removing both reconstruction window 812 and 816 results in a deficient data for reconstruction purposes, whereas deleting 812 and relocating 816 as described above may lead to a suboptimal correction. As an alternative solution, a new reconstruction phase of 45% corresponding to windows 1002, 1004 and 1008, is recommended as shown in FIG. 10. This now enables window 1006 belonging to premature cycle 836 to be removed.

Other aspects are now described.

In the illustrated embodiment, the operator identifies the premature heart cycle within the ECG signal. In an alternative embodiment, the processing component 132 automatically identifies anomalous heart cycles via a premature heart cycle detector 156. In one instance, the processing component 132 prompts the operator for confirmation. In another instance, an automatically identified anomalous heart cycle is automatically considered to be an anomalous heart cycle.

In the illustrated embodiment, the operator provides a desired cardiac phase. In an alternative embodiment, the processing component 132 automatically recommends reconstruction windows and/or a reconstruction phase based on the ECG signal and anomalous signal without user input regarding a desired cardiac phase.

In another embodiment, the processing component 128 automatically locates anomalous heart cycles, selects an optimal reconstruction phase based on an anomalous heart cycle, and generates reconstruction windows for each heart cycle. Optionally, the processing component 128 automatically invokes reconstruction of the reconstruction data set.

In the above description, the new phase is recommended only when there is insufficient data. It is to be appreciated that in an alternative embodiment an additional new phase is always recommended. In one instance, this increases the chances of obtaining a good reconstruction.

The processing component 132, including the analyzing component 136, the windowing component 140, and the recommendation component 144, may be implemented by way of computer readable instructions which, when executed by a computer processor(s), cause the processor(s) to carry out the described techniques. In such a case, the instructions are stored in a computer readable storage medium associated with or otherwise accessible to the relevant computer.

Note also that the described techniques need not be performed concurrently with the data acquisition. They may also be performed using a computer (or computers) which are associated with the scanner 100; they may also be located remotely from the scanner 100 and access the relevant data over a suitable communications network such as a HIS/RIS system, PACS system, the internet, or the like.

Applications of the forgoing and variations thereof include, but are not limited to, selecting suitable data for gated CT, magnetic resonance imaging (MRI), nuclear cardiology and three-dimensional (3D) echo studies.

The invention has been described with reference to the preferred embodiments. Modifications and alterations may occur to others upon reading and understanding the preceding detailed description. It is intended that the invention be con-

Having thus described the preferred embodiments, the invention is now claimed to be:

1. A system, comprising:
a windowing component that receives an ECG signal that includes a premature heart cycle and previously acquired x-ray projection data of a beating heart, wherein the ECG signal is time-synchronized with the previously acquired x-ray projection data of the beating heart, and wherein the windowing component positions a first reconstruction window within a first heart cycle to correspond to a desired cardiac phase of the previously acquired x-ray projection data when the premature heart cycle causes the first reconstruction window to correspond to a different cardiac phase; and
a reconstructor that reconstructs projection data corresponding to a plurality of reconstruction windows from different cardiac cycles to generate image data indicative of the desired phase of the heart.

2. The system of claim 1, wherein the windowing component repositions the first reconstruction window in terms of time relative to a reference signal within the first heart cycle when a first time interval from the reference signal to the first reconstruction window is less than a second time interval from the reference signal to the premature heart cycle.

3. The system of claim 1, wherein the windowing component removes the first reconstruction window when a first time interval from the reference signal to the first reconstruction window is greater than a second time interval from the reference signal to the premature heart cycle.

4. The system of claim 3, further including a recommendation component, wherein the recommendation component recommends a different phase that ensures that the first time interval from the reference signal to the first reconstruction window is less than the second time interval from the reference signal to the premature heart cycle.

5. The system of claim 1, wherein the first heart cycle is the premature heart cycle.

6. The system of claim 5, wherein the windowing component attempts to remove the first reconstruction window on condition that no data gap occurs.

7. The system of claim 5, wherein the windowing component repositions the first reconstruction window in terms of time relative to a reference signal within the first heart cycle when the premature heart cycle is an atrial extrasystole.

8. The system of claim 5, wherein the windowing component repositions the first reconstruction window in terms of time relative to a reference signal in a subsequent heart cycle when the premature heart cycle is a ventricular extrasystole.

9. The system of claim 8, further including a console, wherein an operator provides an input via the console that confirms or rejects the recommended cardiac phase for reconstruction.

10. The system of claim 1, further including a recommendation component, wherein the recommendation component recommends a second phase for reconstruction when the second phase has a relatively higher probability of having sufficient data for reconstruction after removing a reconstruction window due to the premature heart cycle.

11. The system of claim 1, further including a console, wherein an operator provides an input via the console that identifies the premature heart cycle within the ECG signal.

12. The system of claim 1, comprising:
an analysis component that determines if the premature heart cycle causes an affect on the reconstruction window and that, in response to the premature heart cycle causing the affect, determines an extent of the affect, wherein, in response to the premature heart cycle causing an affect on the reconstruction window, the windowing component moves the first reconstruction window, and wherein, in response to the premature heart cycle not causing an affect on the reconstruction window, the reconstructor reconstructs at least part of the x-ray projection data.

13. A system, comprising:
a windowing component that deletes a first reconstruction window that corresponds to a suboptimal cardiac phase of previously acquired x-ray projection data of a beating heart due to an anomalous signal in an ECG signal, wherein the ECG signal is mapped in time with the previously acquired x-ray projection data of the beating heart over a plurality of heart cycles, and wherein the windowing component adds a replacement reconstruction window to optimize the reconstruction data set based on the anomalous signal and available previously-acquired projection data; and
a reconstructor that reconstructs the reconstruction data set to generate image data indicative of the desired phase of the heart.

14. The system of claim 13, wherein the anomalous signal is a premature heart beat.

15. The system of claim 13, comprising a recommendation component that recommends the replacement reconstruction window.

16. The system of claim 13, wherein the windowing component automatically adds the replacement reconstruction window.

17. The system of claim 13, further including an anomalous signal finder that automatically locates and identifies the anomalous signal in the ECG signal.

18. The system of claim 13, wherein the windowing component moves at least a second reconstruction window within a heart cycle to correspond to the desired cardiac phase when the anomalous signal causes the second reconstruction window to correspond to a different cardiac phase.

19. The system of claim 13, wherein the windowing component adds a second reconstruction window if a first product of a time interval from a previous normal reconstruction window to a subsequent normal reconstruction window and a speed of a support in a longitudinal direction is greater than a second product of a collimation of an x-ray beam and an x-ray source rotation time divided by the time interval.

20. A system, comprising:
a recommendation component that recommends a reconstruction window for a cardiac phase within a plurality of previously acquired successive heart cycles based on an ECG signal and an arrhythmia therein, wherein the ECG signal is obtained while concurrently scanning a beating heart with a computed tomography scanner; and
a reconstructor that reconstructs data corresponding to the data for each cycle corresponding to the reconstruction window.

21. The system of claim 20, wherein the reconstruction window corresponds to a generally motionless state of the heart.

22. The system of claim 20, wherein the reconstruction window corresponds to data having a relatively high probability of having no data gaps after removing a reconstruction window due to the arrhythmia.

23. The system of claim 20, wherein an operator selects an initial cardiac phase and the recommended reconstruction window corresponds to a different cardiac phase.

24. The system of claim 20, wherein the recommendation component recommends at least a second reconstruction window that corresponds to a different cardiac phase.

25. A system, comprising:
- a windowing component that automatically repositions or removes a first reconstruction window for a heart cycle based on a premature heart cycle within an ECG that is signal synchronized with previously acquired x-ray projection data of a beating heart;
- a recommendation component that automatically recommends at least one additional reconstruction window based on the premature heart cycle; and
- a reconstructor that reconstructs data corresponding to the reconstruction windows.

26. The system of claim 25, wherein the reconstruction data represents an optimal set of data in that it includes a complete set of data for reconstruction and reduces artifact introduced from reconstructing data corresponding to different cardiac phases.

27. A method, comprising:
- receiving an ECG signal including a premature heart cycle, wherein the ECG signal is time-synchronized with previously acquired x-ray projection data of a beating heart over multiple heart cycles;
- relocating a first reconstruction window within a first heart cycle that corresponds to data other than a desired cardiac phase due to the premature heart cycle, wherein each of a plurality of heart cycles includes a reconstruction window; and
- reconstructing the previously acquired projection data corresponding to the plurality of reconstruction windows to generate image data indicative of the desired phase of the heart.

28. The method of claim 27, further including relocating a second reconstruction window within the premature heart cycle relative to a reference signal in the premature heart cycle in terms of time or relative to a reference signal in a next heart cycle in terms of time, depending on type of premature heart cycle.

29. The method of claim 27, further including removing the first reconstruction window.

30. The method of claim 27, further including recommending reconstructing data for a second different cardiac phase.

31. The method of claim 27, further including adding at least one reconstruction window that corresponds to a different cardiac phase.

* * * * *